(12) United States Patent
Molina

(10) Patent No.: US 11,259,657 B1
(45) Date of Patent: Mar. 1, 2022

(54) ANTI-SNORING PILLOW AND PILLOWCASE SYSTEM

(71) Applicant: Jose B Molina, Miami, FL (US)

(72) Inventor: Jose B Molina, Miami, FL (US)

( * ) Notice: Subject to any disclaimer, the term of this patent is extended or adjusted under 35 U.S.C. 154(b) by 0 days.

(21) Appl. No.: 17/313,788

(22) Filed: May 6, 2021

(51) Int. Cl.
*A47G 9/10* (2006.01)
*A61F 5/56* (2006.01)
*A47G 9/02* (2006.01)
*A47G 9/00* (2006.01)

(52) U.S. Cl.
CPC ......... *A47G 9/1081* (2013.01); *A47G 9/0253* (2013.01); *A61F 5/56* (2013.01); *A47G 2009/001* (2013.01); *A47G 2009/1018* (2013.01)

(58) Field of Classification Search
CPC ............... A47G 9/1081; A47G 9/0253; A47G 2009/1018; A47G 2009/001; A61F 5/56
See application file for complete search history.

(56) References Cited

U.S. PATENT DOCUMENTS

| | | | | |
|---|---|---|---|---|
| 2,552,476 A | * | 5/1951 | Barton | A47C 7/021 5/653 |
| 2,940,088 A | * | 6/1960 | Boos | A47G 9/10 5/636 |
| 3,608,157 A | * | 9/1971 | Molt | B68G 7/08 24/102 T |
| 3,829,935 A | * | 8/1974 | Critchfield | A47C 31/026 24/114.3 |
| 3,856,353 A | * | 12/1974 | Morrison | A47C 31/026 297/452.56 |
| 4,080,675 A | * | 3/1978 | Kanowsky | A47C 27/15 297/452.58 |
| 4,218,792 A | * | 8/1980 | Kogan | A47G 9/109 5/636 |
| 5,363,524 A | * | 11/1994 | Lang | A47G 9/1081 5/640 |
| 5,457,832 A | * | 10/1995 | Tatum | A61F 5/01 5/636 |
| 6,009,577 A | * | 1/2000 | Day | A47C 7/383 5/636 |
| 6,742,207 B1 | * | 6/2004 | Brown | A47G 9/1081 5/636 |
| 6,751,818 B2 | * | 6/2004 | Troop | A61G 7/072 5/630 |

(Continued)

FOREIGN PATENT DOCUMENTS

| | | | | |
|---|---|---|---|---|
| EP | 3656255 A1 | * | 5/2020 | A61F 5/56 |
| WO | WO-2015119403 A1 | * | 8/2015 | A61G 7/07 |

*Primary Examiner* — Myles A Throop
(74) *Attorney, Agent, or Firm* — Ruben Alcoba, Esq.

(57) ABSTRACT

An anti-snoring pillow is designed to make side sleepers more comfortable for longer periods of time. The anti-snoring pillow is designed to cradle and support the jaw of a user, and to minimize the user's ear discomfort when the user uses the pillow. The anti-snoring pillow comprises a pillow that defines a semicircular central cavity that concaves toward a central ear cavity, a through hole that is defined on a central section of the central ear cavity, a left jaw support and a right jaw support that are defined on a lower horizontal section of the semicircular central cavity, and a concaved neck support that is defined between the left jaw support and the right jaw support that runs toward the central ear cavity. The pillow is covered with a fitted pillowcase that is locked onto the pillow.

7 Claims, 5 Drawing Sheets

(56) References Cited

U.S. PATENT DOCUMENTS

| | | | | |
|---|---|---|---|---|
| 7,082,633 B1* | 8/2006 | Maarbjerg | ............... | A47G 9/10 5/636 |
| 8,161,588 B1* | 4/2012 | Anson | .................... | A47G 9/109 5/636 |
| 8,707,485 B1* | 4/2014 | Conley | ................. | A47G 9/109 5/636 |
| 2010/0175193 A1* | 7/2010 | Oh | ....................... | A47C 31/004 5/638 |
| 2012/0180220 A1* | 7/2012 | Popitz | ................. | A47G 9/1081 5/638 |
| 2013/0298333 A1* | 11/2013 | Chen | .................... | A47G 9/1081 5/636 |
| 2014/0000035 A1* | 1/2014 | Berg | ....................... | A47G 9/10 5/636 |
| 2015/0265075 A1* | 9/2015 | Liu | ........................... | A61F 5/56 5/640 |
| 2016/0345747 A1* | 12/2016 | Selle | ................... | A47C 31/026 |
| 2017/0127855 A1* | 5/2017 | Wootten, Jr. | ......... | A47G 9/0261 |
| 2018/0317677 A1* | 11/2018 | Genao | .................... | H04R 1/028 |
| 2019/0298006 A1* | 10/2019 | Dagostino | ............. | A47G 9/0261 |
| 2020/0037797 A1* | 2/2020 | Rosenberg | ............... | A47G 9/10 |
| 2020/0214481 A1* | 7/2020 | Sexton | ................. | A61H 23/00 |
| 2021/0186236 A1* | 6/2021 | Yuan | .................... | A47G 9/0253 |

* cited by examiner

ANTI-SNORING PILLOW AND PILLOWCASE SYSTEM

BACKGROUND OF THE INVENTION

The present invention relates to an anti-snoring pillow and pillowcase system that encourages users to sleep on their sides to prevent snoring.

The present invention is an anti-snoring pillow and pillowcase system, which addresses the problems of snoring. More particularly, the present invention relates to an anti-snoring pillow, which embodies a combination of essential physical characteristics that collectively serve to allow a user to sleep comfortably on his or her side.

Medical research and studies have found that when people sleep on their sides that they substantially reduce the frequency and the intensity and/or loudness of their snoring.

The anti-snoring pillow of the present invention is designed to allow a user's ear to fall within a section of the pillow that defines an ear aperture that minimizes the user's ear from contacting the pillow. The positioning of the user's ear within the aperture reduces any ear discomfort the user would normally suffer from if he or she were sleeping on a standard pillow. The present invention also defines a jaw cradle support that keeps a user's mouth from opening when the user uses the anti-snoring pillow. The design of the present invention allows a user to remain on his or her side for longer periods.

Typically, many individuals snore while sleeping: snoring is the hoarse or harsh sound which occurs when air flows past relaxed tissues in the throat, causing the tissues to vibrate as one breathes. Usually, snoring occurs while the individual is in a deep sleep, at that point in time the individual's facial muscles are relaxed which causes the individual's jaw and mouth to open. Clinical institutions report that dry mouth and bad breath worsen when people sleep with their mouths open. As our muscles relax when falling asleep, the jaw tends to collapse downward due to gravity, and our mouths open. When we breathe through our mouths, snoring normally commences.

The sleep industry has produced and promoted drugs, supplements, pillows, mattresses, straps, and other devices to help people who snore. Yet interestingly, none of the drugs or products are designed to address the problem of sleeping on one's back.

The present invention addresses the need of having an anti-snoring pillow that will minimize snoring.

SUMMARY

The present invention is an anti-snoring pillow that will reduce snoring. The anti-snoring pillow is designed to make side sleepers more comfortable for longer periods of time. The invention is designed to cradle and support the jaw of a user and to minimize the user's ear discomfort when the user uses the pillow.

The anti-snoring pillow comprises a pillow that defines a semicircular central cavity that concaves toward a central ear cavity, a through hole that is defined on a central section of the central ear cavity, a left jaw support and a right jaw support that are defined on a lower horizontal section of the semicircular central cavity, and a concaved neck support that is defined between the left jaw support and the right jaw support that runs toward the central ear cavity. The pillow is covered with a fitted pillowcase that is locked onto the pillow.

The semicircular central cavity allows for equal level of comfort for left-side and right-side sleepers. The concaved neck support supports the neck of a user when the user's head is placed on the anti-snoring pillow. The central ear cavity is designed to allow a user's ear to fall within the central ear cavity when the user is side sleeping. The positioning of the central ear cavity minimizes ear discomfort that a user would suffer when side sleeping.

The main cavity also contains a cradle area that supports the user's jaw. The cradle area addresses the gravity's effect on the jaw that forces the mouth to open when one falls asleep; the cradle area is uniquely contoured to gently cradle and support the user's jaw and keep the user's mouth closed. The left jaw support and the right jaw support can be sized to accommodate the user's jaw features.

An object of the present invention is to provide an anti-snoring pillow.

Another object of the present invention is to provide an anti-snoring pillow that is made to accommodate a side sleeper.

Yet another object of the present invention is to provide an anti-snoring pillow that will reduce ear discomfort when side sleeping.

Yet still another object of the present invention is to provide a fitted pillowcase that will be locked in place on the anti-snoring pillow.

DRAWINGS

These and other features, aspects, and advantages of the present invention will become better understood with regards to the following description, appended claims, and drawings where:

DESCRIPTION

Figure 1:
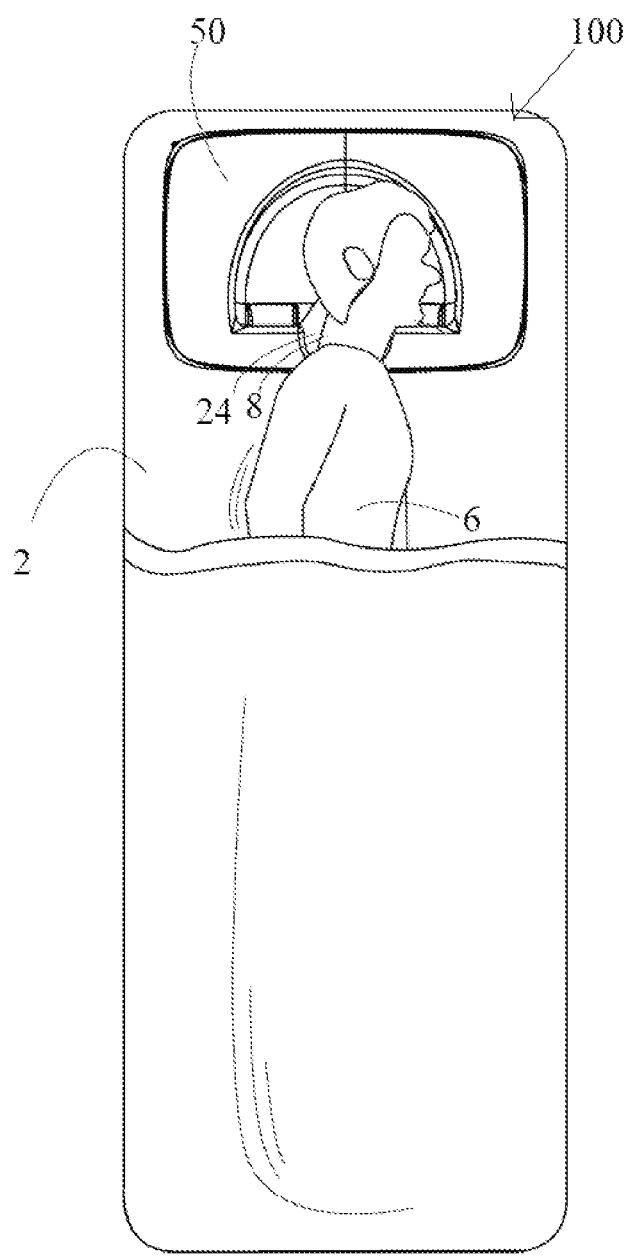
FIG. 1 is a top general view of the anti-snoring pillow showing a user using the anti-snoring pillow.

As seen in FIGS. 1-7, the present invention is an anti-snoring pillow that reduces snoring.

The anti-snoring pillow 100 comprises a pillow 10 that defines a semicircular central cavity 12 that concaves toward a central ear cavity 14. A through hole 16 that is defined on a central section 14a of the central ear cavity 14. A left jaw support 20 and a right jaw support 22 that are defined on a lower horizontal section 12a of the semicircular central cavity 12 and the left jaw support 20 defines a left cradle 300 and the right jaw support 22 defines a right cradle 302, the left cradle 300 and the right cradle 302 are configured to keep a jaw of a user at an angle that is about ninety degree from the user's neck when the user rests either the user's left side or right side of his or her face on the pillow 10, the left cradle 300 and the right cradle 302 each comprise of an upward curved chin support portion 304 that are configured to maintain the chin of the user in a fixed position, and a concave neck support 24 is defined between the left jaw support 20 and the right jaw support 22 that runs toward the central ear cavity 14, the left jaw support 20 and the right jaw support 22 are colinear to each other, the left jaw support 20 is perpendicular to a left outermost edge 24a of the concave neck support 24 and the right jaw support 22 is perpendicular to a tight outermost edge 24b of the concave neck support 24, the concave neck support 24 defines a slope 24c that falls inward toward the through hole 16 from an upper lower section 24d of the concave neck support 24.

In an embodiment of the present invention, the anti-snoring pillow 100 comprises of a fitted pillowcase 50 that defines an end lock 52 on a lower portion 50b of a front side 50a of the fitted pillowcase 50, the fitted pillowcase 50 is placed over the anti-snoring pillow 100 so that the end lock aligns 52 with the through hole 16 of pillow 10, the end lock 52 is configured to pass through the through hole 16 of the pillow 10 and then is configured to lock into a lock receiver 54 that is defined on a rear side 50c of the fitted pillow case 50. In a preferred embodiment, the end lock 52 is a button 52 and the lock receiver 54 is a slit 54.

In preferred embodiments of the present invention, the pillow is made of a memory foam material.

In preferred embodiments of the present invention, the fitted pillowcase is made of an anti-allergic cotton material.

In embodiments of the present invention, the cotton material is a blend of the cotton material and of an elastic material.

In preferred embodiments of the present invention, the pillow is rectangularly shaped.

Figure 3:
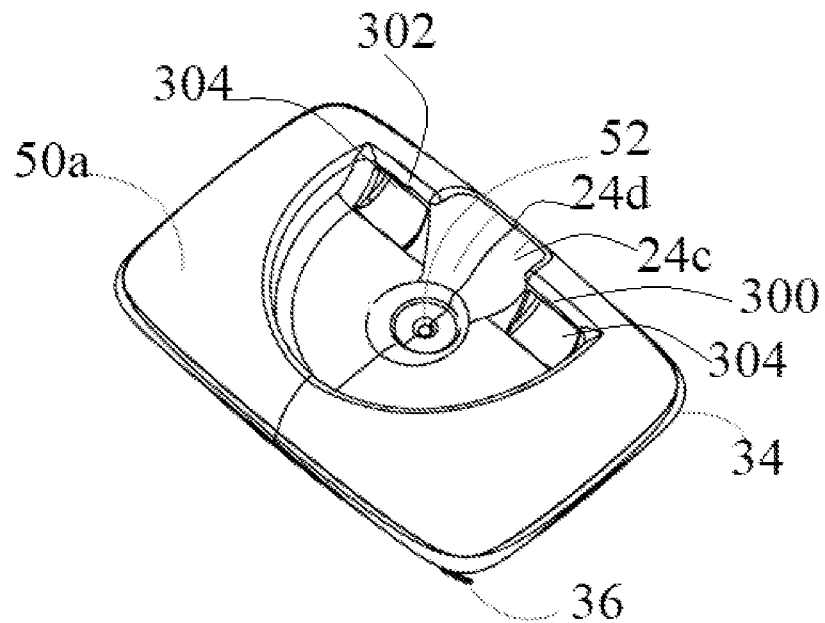
FIG. 3 is a back side perspective view of the anti-snoring pillow, this view shows the pillowcase.

As seen in FIG. 1, the user of the present invention is seen laying on his or her side 6 on top of a bed 2, using the present invention 100. As the user's neck is turned on his or her side 8, their neck is being supported by the concaved neck support 24. The placement of the user's neck within the concaved neck support 24 reduces the normal stress placed on the neck when the user sleeps on his side. The user's jaw rests in a closed position when using the present invention. The user's jaw rests, as seen in FIG. 3, within the left jaw support 20 or right jaw support 22. This gives the user's jaw the right amount of resistance it needs to keep the mouth from opening when the user uses the anti-snoring pillow 100. By maintaining the mouth of the user closed, snoring is reduced.

Figure 2:
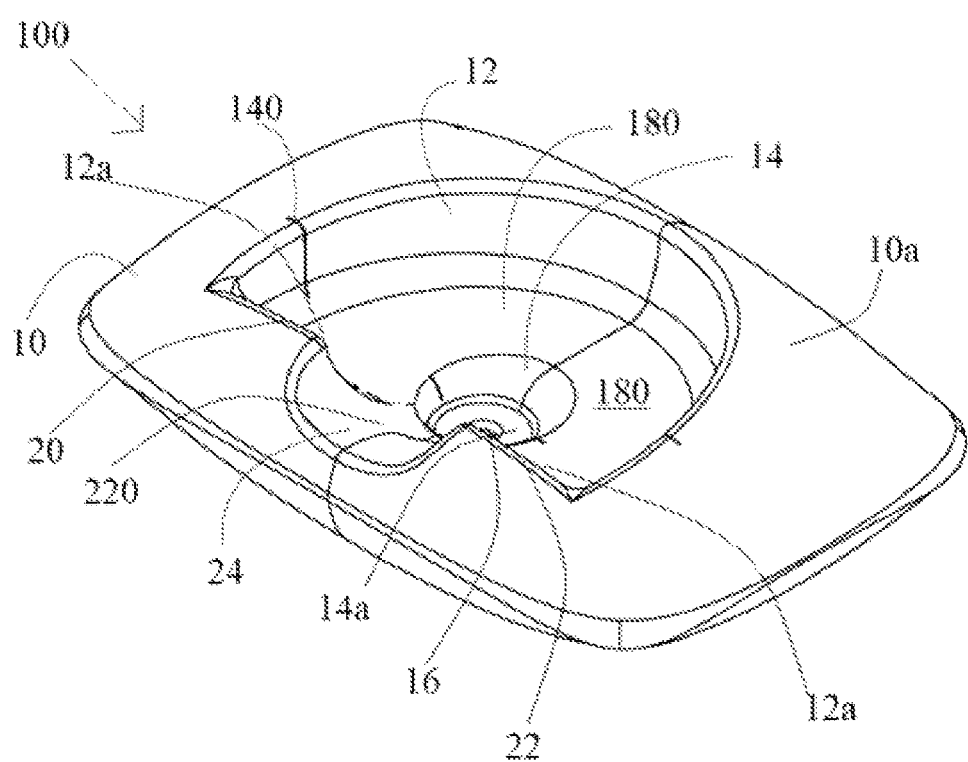
FIG. 2 is a front side perspective view of the anti-snoring pillow, this view does not show the pillowcase of the present invention.

As shown in FIG. 2, the semicircular central cavity 12 allows the user to sleep comfortably on his or her side and rest his or her head in the semicircular central cavity 12. The concaved neck support 24 provides support to the user's neck. The concaved neck support 24 gradually curves down 220 to accommodate the user's jaw until it lines up with a flat surface 180 which supports the general side of the user's face. The central ear cavity 14 allows the user to rest their ear inside the central ear cavity 14, this way while the rest of the user's head's weight has support on the flat surface 180, the ear of the user rests inside the central ear cavity 14 without stressing the weight of the user's head on the user's ear. Placing the user's ear within the central ear cavity 14 reduces ear pressure and earache and diminishes pain or discomfort on the ear when sleeping on one's side for long periods of time. The present invention can be designed to allow the left jaw support 20 and the right jaw support 22 to be expandable. The semicircular central cavity 12 can be designed to be expandable via an adjustor 140.

FIG. 3 shows the fitted pillowcase cover 50 which is made from a cotton and stretchable material. The fitted pillowcase cover covers and expands into the surfaces and shapes of the pillow 10. The pillowcase has an expandable edge 34 which helps to better fit the pillow's shape. It, could be taken off the pillow for washing and cleaning using an opening which could be opened and closed using a zipper 36.

Figure 4:
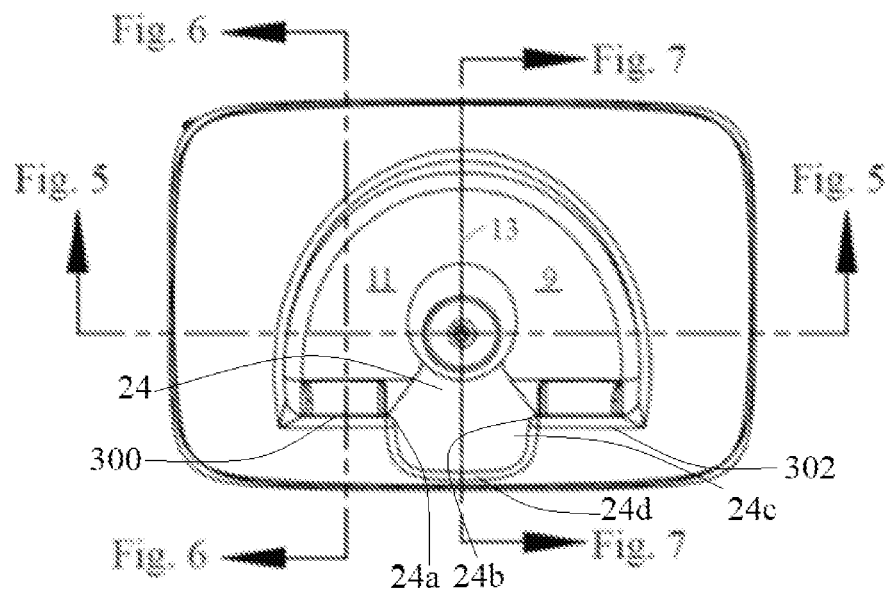
FIG. 4 is a plan view of the anti-snoring pillow showing the cross-section lines of the present invention.

FIG. 4 Shows the plan view of the present invention with a symmetrical design of the pillow's general shape and more particularly the semicircular central cavity 12 of the present invention. The virtual symmetry, line 13, splits the present invention to a right part 9 and a left part 11. In this way the user can use the pillow for right side or left side sleeping.

Figure 5:
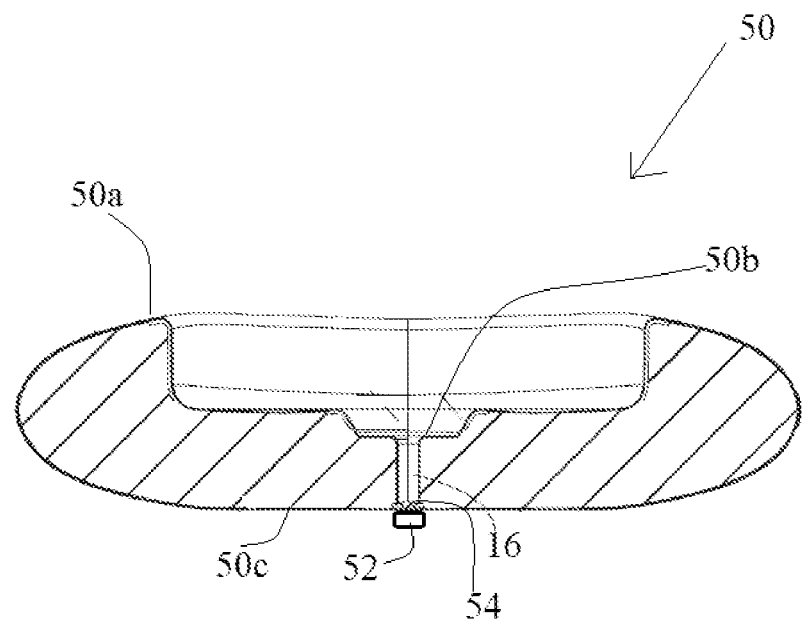
FIG. 5 is a front cross section view of the anti-snoring pillow showing a pillowcase attachment mechanism.

FIG. 5 reveals a front cross section view that shows how the front of the fitted pillowcase is secured or buttoned to the back of the fitted pillowcase.

Figure 6:
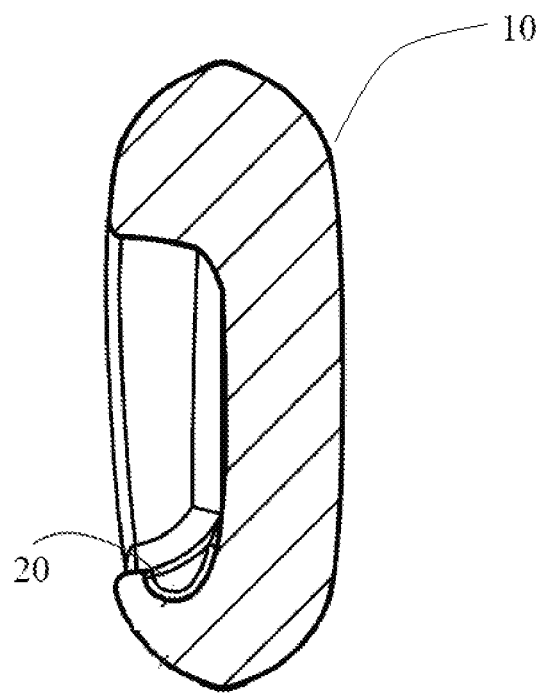
FIG. 6 is a side cross section view of the anti-snoring pillow revealing the chin and jaw support structure of the anti-snoring pillow.

FIG. 6 shows a side cross section view of the left jaw support 22 and the right jaw support 22.

Figure 7:
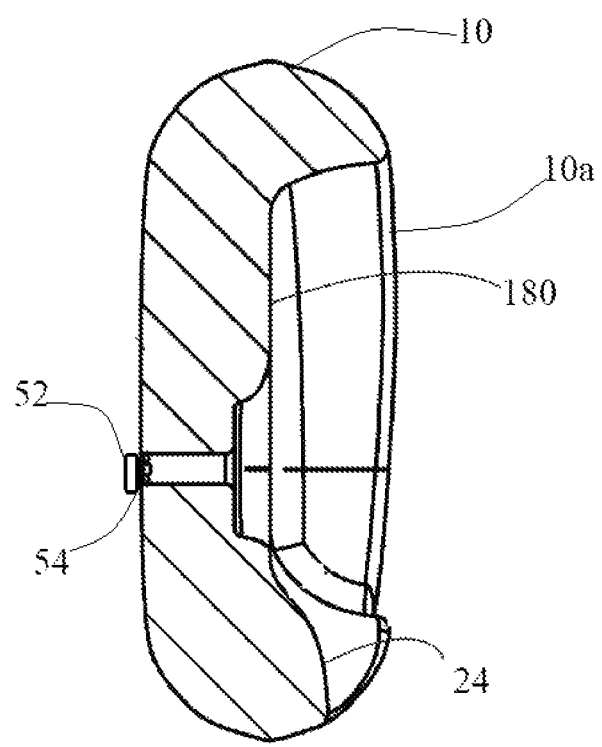
FIG. 7 is a side cross middle section view of the anti-snoring pillow revealing a neck support structure of the present invention.

FIG. 7 Shows a side cross section view revealing the concaved neck support 24, itis located lower and indented compared, to a top surface 10a of the pillow 10. This allows the user to have an ergonomic support for their neck when sleeping on their side, it is located higher compared to the flat area 180 of the pillow.

An advantage of the present invention is that it provides an anti-snoring pillow.

Another advantage of the present invention is that it provides an anti-snoring pillow that accommodates side sleepers.

Yet another advantage of the present invention is that it provides an anti-snoring pillow that reduces ear discomfort when side sleeping.

Yet still another advantage of the present invention is that it provides a fitted pillowcase that locks in place onto the anti-snoring pillow.

While the inventor's above description contains many specificities, these should not be construed as limitations on the scope, but rather as an exemplification of several preferred embodiments thereof. Many other variations are possible. Accordingly, the scope should, be determined not by the embodiments illustrated, but by the specification, the drawings, and the appended claims and their legal equivalents.

What is claimed is:

1. An anti-snoring pillow that reduces snoring, the anti-snoring pillow comprises a pillow that defines a semicircular central cavity that concaves toward a central ear cavity, a through hole that is defined on a central section of the central ear cavity, a left jaw support and a right jaw support that are defined on a lower horizontal section of the semicircular central cavity and the left jaw support defines a left cradle and the right jaw support defines a right cradle, the left cradle and the right cradle are configured to keep a jaw of a user at an angle that is about ninety degree from the user's neck when the user rests either the user's left side or right side of his or her face on the pillow, the left cradle and the right cradle each comprise of an upward curved chin support portion that are configured to maintain the chin of the user in a fixed position, and a concave neck support that is defined between the left jaw support and the right jaw support that runs toward the central ear cavity, the left jaw support and the right jaw support are colinear to each other, the left jaw support is perpendicular to a left outermost edge of the concave neck support and the right jaw support is perpendicular to a right outermost edge of the concave neck support, the concave neck support defines a slope that falls inward toward the through hole from an upper lower section of the concave neck support; wherein, the upper lower section of the concave neck support extends to an outer perimeter of the pillow, such that the pillow is configured to keeps a user's mouth from opening when the user uses the anti-snoring pillow and configured to reduce normal stresses placed on the user's neck when the user sleeps on his side.

2. The anti-snoring; pillow that reduces snoring of claim 1, wherein the pillow is rectangularly shaped.

3. The anti-snoring pillow that reduces snoring of claim 1, the anti-snoring; pillow comprises of a fitted pillowcase that defines an end lock on a lower portion of a front side of the fitted pillowcase, the fitted pillowcase is placed over the anti-snoring pillow so that the end lock aligns with the through hole of pillow, the end lock is configured to pass through the through hole of the pillow and then is configured to lock into a lock receiver that is defined on a rear side of the fitted pillow case.

4. The anti-snoring pillow that reduces snoring of claim 3, wherein the pillow is made of a memory foam material.

5. The anti-snoring pillow that reduces snoring of claim 4, wherein the fitted pillowcase is made of an anti-allergic cotton material.

6. The anti-snoring pillow that reduces snoring of claim 5, wherein the cotton material is a blend of the cotton material and of an elastic material.

7. The anti-snoring pillow that reduces snoring of claim 3, wherein the end lock is a button and the lock receiver is a slit.

\* \* \* \* \*